United States Patent [19]
Thatcher

[11] Patent Number: 4,738,266
[45] Date of Patent: Apr. 19, 1988

[54] APNOEA MONITOR

[76] Inventor: John B. Thatcher, 3860 Pendiente Cir., Bldg. CD-105, San Diego, Calif. 92124

[21] Appl. No.: 492,648

[22] Filed: May 9, 1983

[51] Int. Cl.$^4$ .............................................. A61B 5/08
[52] U.S. Cl. ..................................... 128/719; 128/664
[58] Field of Search ............... 128/664, 716, 719, 903, 128/904; 340/573, 579, 600; 422/84

[56] References Cited
U.S. PATENT DOCUMENTS

| | | | |
|---|---|---|---|
| 3,036,568 | 5/1962 | Stark | 128/664 |
| 4,011,859 | 3/1977 | Frankenberger | 128/719 |
| 4,066,072 | 1/1978 | Cummins | 128/903 |
| 4,350,166 | 9/1982 | Mobarry | 128/664 |

Primary Examiner—Lee S. Cohen
Attorney, Agent, or Firm—Keith D. Beecher

[57] ABSTRACT

An apnoea monitor for preventing sudden infant death syndrome (SIDS). The exhaled breath of the infant is collected in a hood. A source of infrared energy emits infrared energy into the hood. So long as the infant is breathing, the carbon dioxide in its breath absorbs a portion of the infrared energy in the hood. Should the infant stop breathing, an infrared detector responds to the resulting increase in infrared energy to activate an alarm so as to enable the attendant personnel to take appropriate life saving action.

8 Claims, 5 Drawing Sheets

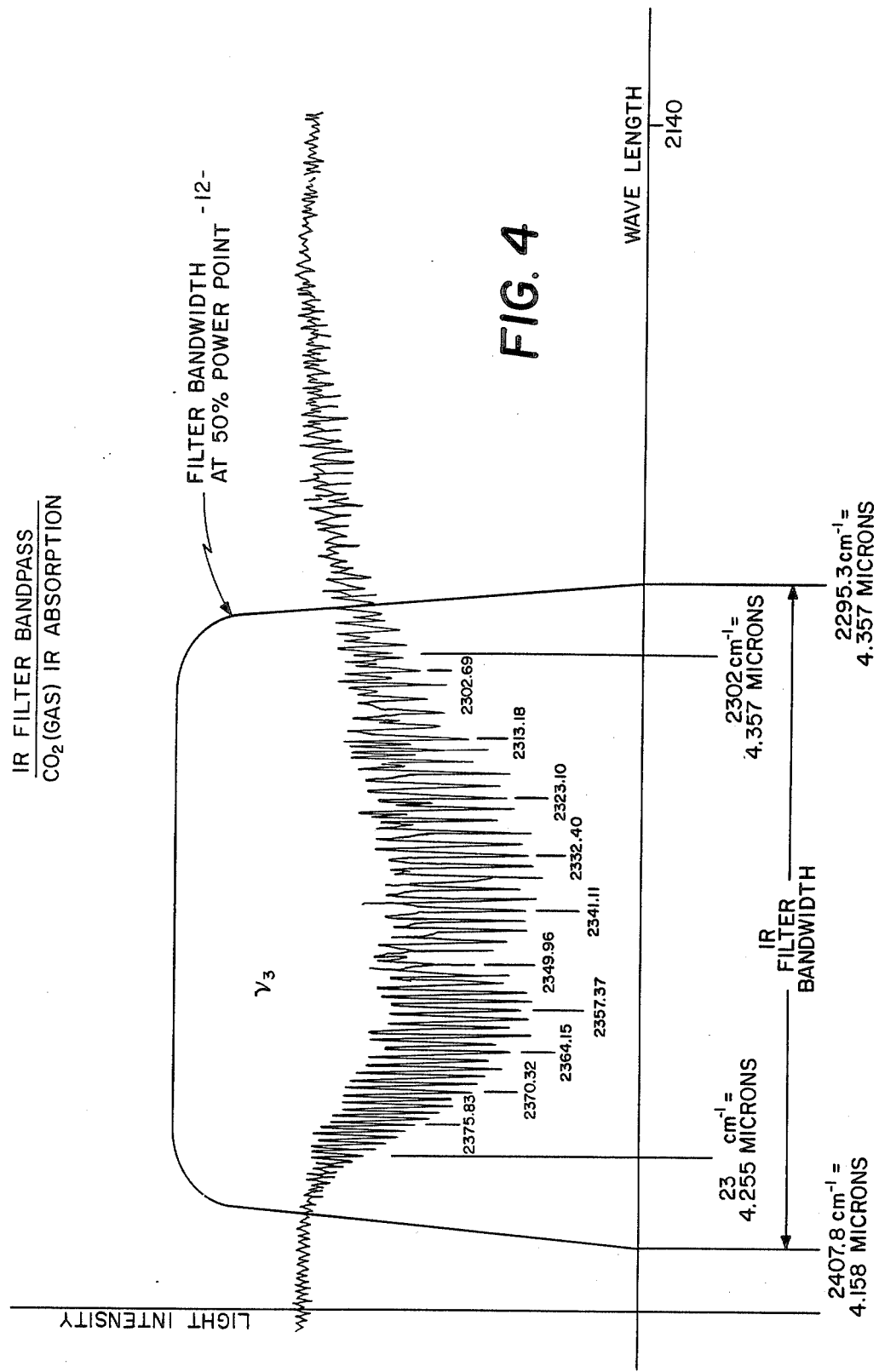

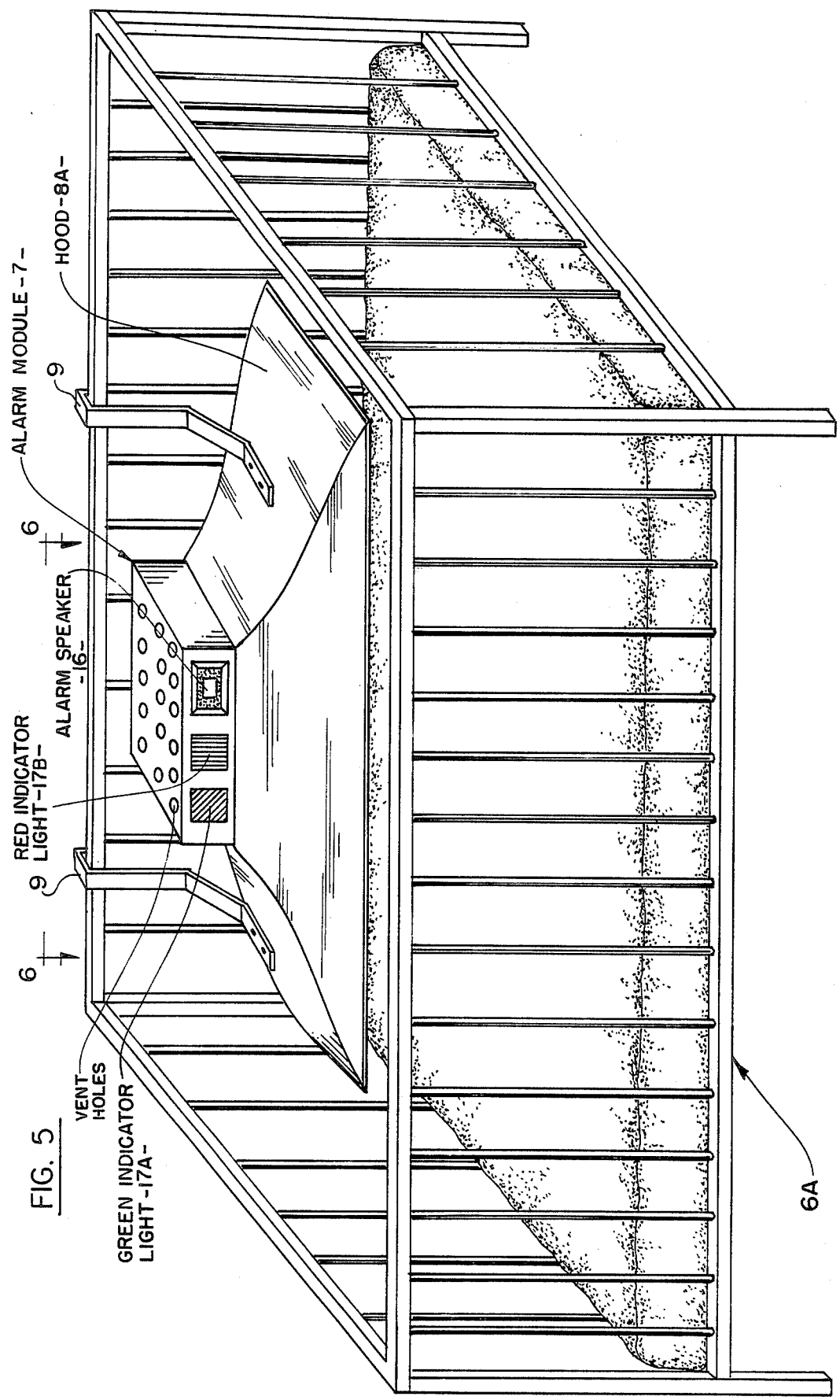

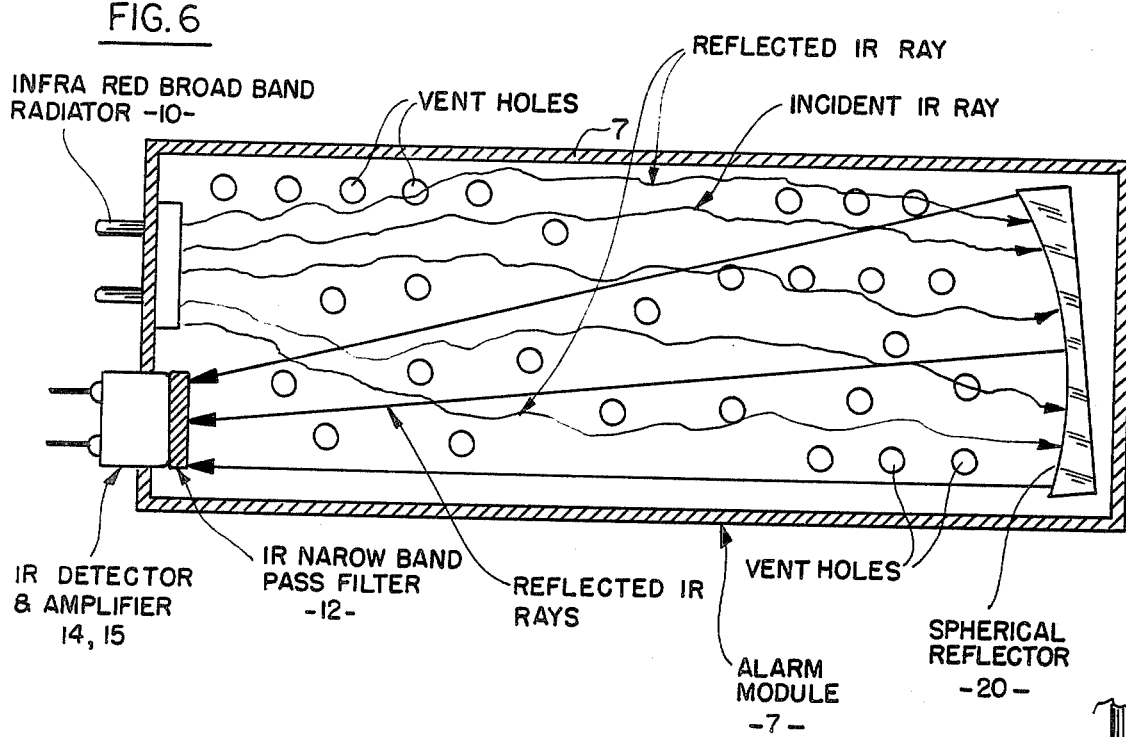
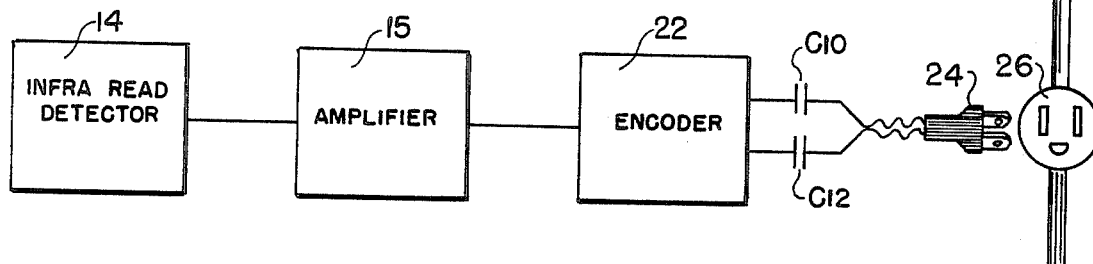
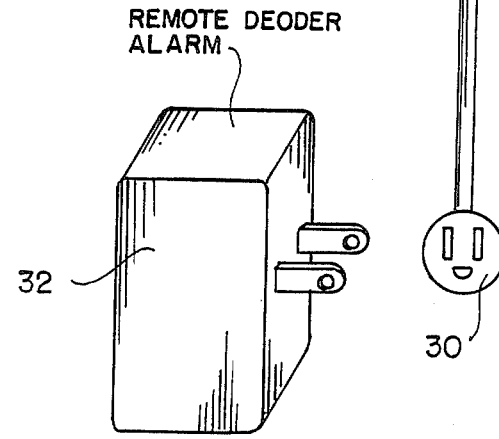

APNOEA MONITOR

BACKGROUND OF THE INVENTION

There are an estimated 10,000–15,000 deaths in the United States each year due to sudden infant death syndrome (SIDS), making it the most frequent cause of death in the first year of life. Many hypotheses have been formulated to explain its etiology. Most of the easily recognized post-mortem abnormalities in the victims are in the lungs and they have usually been interpreted as evidence of a sudden catastrophic event in an otherwise normal infant. Years of speculation about the nature of the catastrophic event have been unfruitful because the easily recognized post-mortem abnormalities give few clues to the dynamic events surrounding the deaths.

The term "apnoea" is often used in conjunction with SIDS as a symptom as well as a cause. Apnoea may be defined as a pause in the infant's breathing equal to or exceeding six seconds. Short periods of apnoea during sleep are normal during infancy while prolonged periods are abnormal. In 1972 Steinschneider (Pediatrics 50:646-654, 1972) reported that several SIDS victims had prolonged periods of apnoea during sleep before death.

In an attempt to combat SIDS, monitoring systems have been proposed in the past which react to any period of apnoea in the sleeping infant. Although some of the indications may be false alarms due to normal periods of apnoea by the infant, in any event, the parents or attending nurses are alerted by the monitors whenever the infant stops breathing, even for a short period.

The prior art monitors, however, suffer from a disadvantage in that they usually involve placing electrodes on the infant with leads extending to the monitoring equipment. These electrodes and leads are a source of discomfort to the infant and inhibit normal sleep. Moreover, the electrodes themselves often cause skin irritation. Another problem is the fact that such prior art systems exhibit failures with no detectable electrical fault and, accordingly, are believed to be unreliable.

The use of infrared energy to detect if an infant has stopped breathing has been suggested in the prior art. The exhalations of the infant include large quantities of carbon dioxide. Carbon dioxide is absorbent to the long wave infrared radiation. The detector detects the difference in the infrared radiation due to the absorption incident to the exhalations of the infant. The resulting signal is applied to a suitable alarm circuit to indicate an interruption of the exhalation exceeding a predetermined time interval.

A non-contacting apnoea detector is disclosed in U.S. Pat. No. 4,350,166. However, the detector relies on infrared radiation from the infant itself, which peaks at 9.6 microns; whereas carbon dioxide is absorbed at 15 microns. This militates substantially against the effectiveness of the prior art device.

The monitoring system of the apnoea monitor of the present invention is simple in its construction, yet it is extremely reliable, and it is capable of detecting apnoea in the infant without any primary or secondary electrical hook-ups to the child itself. As explained briefly above, the apnoea monitoring system of the invention collects the exhaled breath of the infant in an area in which infrared energy is emitted from an infrared source and, through infrared absorption, measures the quantity of carbon dioxide present in the breath. So long as the carbon dioxide is present, the child is breathing. Should apnoea occur and the child stops breathing, the carbon dioxide will disappear and an infrared detector will respond to the resulting rise in the infrared intensity to cause an alarm to be triggered. This permits the attending nurse or parents to take immediate life saving action.

It is accordingly an objective of the present invention to provide an improved simple and inexpensive apnoea monitoring system which detects and continuously monitors actual infant breathing, without any physical contact with the infant itself. The system of the invention is advantageous in that it is highly reliable, it is not subject to failure, and it does not involve complex and inconvenient wire hook-ups which are uncomfortable and disturbing to the infant.

BRIEF DESCRIPTION OF THE DRAWINGS

FIG. 4 are curves showing the absorption of infrared energy by carbon dioxide gas, and which are useful in explaining the operation of the system of the invention;

FIG. 5 is a perspective representation of a second embodiment of the invention;

FIG. 6 is a top sectional view of an alarm module included in the embodiment of FIG. 5; and FIG. 7 is a schematic diagram of a remote alarm system using the domestic power lines.

DETAILED DESCRIPTION OF THE ILLUSTRATED EMBODIMENT

Figure 1:
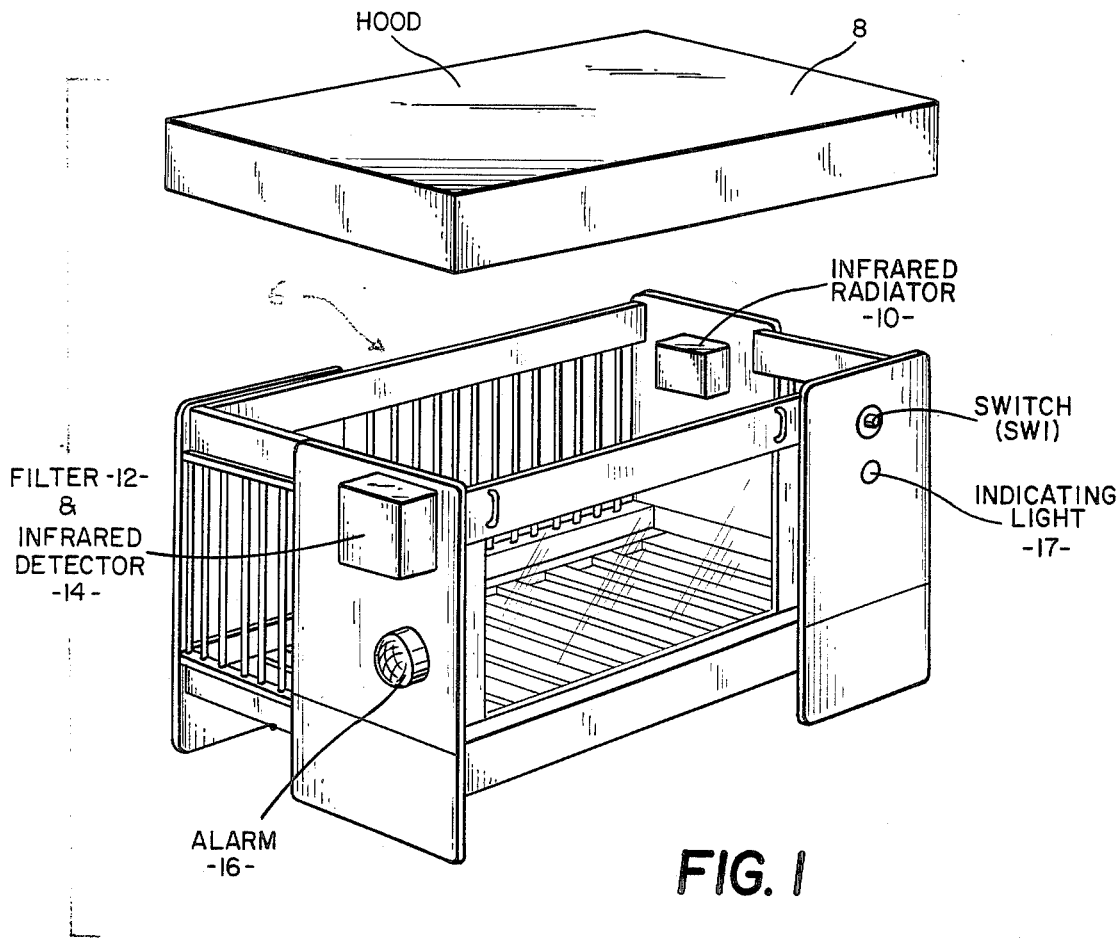
FIG. 1 is a perspective representation of an infant's crib equipped with a system for performing the apnoea monitoring function of the present invention.

The crib shown in FIG. 1 is designated generally 6. The crib is equipped with a hood 8 which may be composed of plastic, or other appropriate material, and which fits over the crib 6 to collect the exhaled breath of an infant sleeping in the crib. An infrared radiator 10 is mounted on one of the headboards of crib 6, and it directs infrared energy to a filter 12 and infrared detector 14 mounted on the opposite headboard.

So long as the infant in the crib is breathing, the carbon dioxide in his exhaled breath absorbs a portion of the infrared energy traveling from the radiator 10 to the detector 14. However, should the infant stop breathing, the carbon dioxide disappears, and no longer absorbs any portion of the infrared energy. Accordingly, the output of detector 14 increases in amplitude and activates an alarm 16. The system is turned on and off by a switch SW1. An indicating light 17 adjacent to the switch is illuminated when the system is operated.

Figure 2:
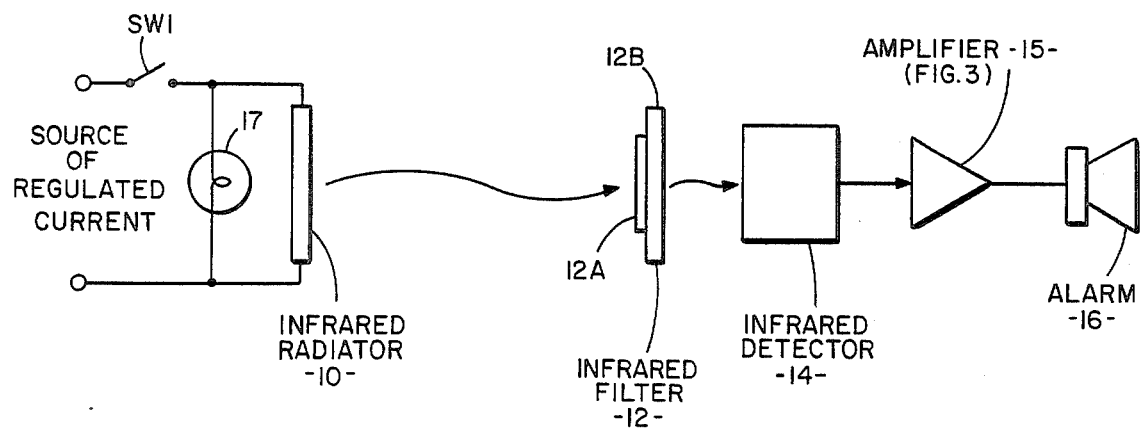
FIG. 2 is a schematic rendition of an apnoea monitoring system in accordance with one embodiment of the invention.

In the schematic diagram of FIG. 2, the infrared radiator 10 is shown as connected through switch SW1 to a source of regulated current. This source, for example, may be activated by the usual alternating current mains, and may also be equipped with a back-up battery which would take over in the event of power failure.

The infrared radiator may be any appropriate black body device which is heated, for example, to 680° K. (407° C.) for maximum infrared radiation at wavelengths in the vicinity of 4 microns. For example, the infrared radiator 10 is heated to provide infrared radiation approximately in the wavelength range of 3–6 microns. This infrared energy is present in the area under hood 8 of FIG. 1, and it takes the form shown in FIG. 4. So long as the infant is breathing, the carbon dioxide in the area under the hood absorbs the infrared energy in the region extending approximately from 4.255–4.344 microns, as shown in FIG. 4.

The infrared energy is passed through a filter 12 to an infrared detector 14. Filter 12 may be an infrared thin film filter of approximately 4.1–4.4 microns in bandwidth, as shown in FIG. 4. The filter material itself, designated 12A in FIG. 2 is mounted on a substrate 12B which exhibits high transmission characteristics to infrared energy.

Figure 3:
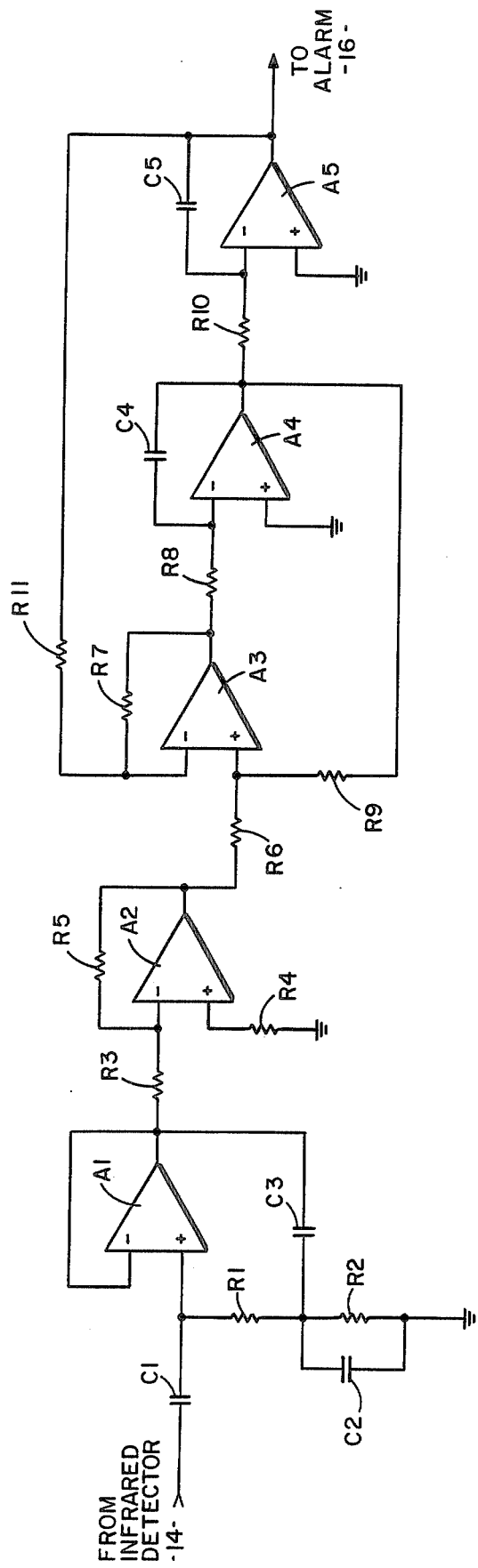
FIG. 3 is a circuit diagram of an amplifier which may be included in the system of FIG. 2.

The output of the infrared detector 14 is amplified by amplifier 15 which is shown in circuit detail in FIG. 3. The output of the amplifier 15 is connected to an appropriate alarm 16. Amplifier 15 may be formed integral with the infrared detector 14.

As shown in FIG. 3, amplifier 15 is made up of five operational amplifiers A1, A2, A3, A4 and A5. Amplifiers A1 and A2 may be of the type designated LM741, and the remaining amplifiers may be on a common integrated circuit chip of the type designated LM324.

The output from the infrared detector 14 is passed through a 0.01 microfarad coupling capacitor C1 to the non-inverting input terminal of amplifier A1. This terminal is connected to a 100 kilo-ohm resistor R1 which in turn is connected to a grounded 100 kilo-ohm resistor R2. A 0.001 microfarad capacitor C2 is connected across resistor R2. The output of amplifier A1 is connected back to the inverting input terminal, and also through a 5 microfarad capacitor C3 to the unction of resistors R1 and R2.

The output of amplifier A1 is also connected through a 1 kilo-ohm resistor R3 to the inverting input terminal of amplifier A2. The non-inverting input terminal of amplifier A2 is connected to a 1 kilo-ohm grounded resistor R4. The output terminal of the amplifier A2 is connected back to the inverting input terminal through a 100 kilo-ohm resistor R5, and through a 1 kilo-ohm resistor R6 to the non-inverting input terminal of amplifier A3. The output terminal of amplifier A3 is connected through a 10 kilo-ohm resistor R7 to the inverting input terminal, and through a 100 kilo-ohm resistor R8 to the inverting input terminal of amplifier A4. The non-inverting input terminal of amplifier A4 is grounded.

The output terminal of amplifier A4 is connected back to the non-inverting input terminal of amplifier A3 through an 18 kilo-ohm resistor R9, and is coupled back to its inverting input terminal through a 0.2 microfarad capacitor C4. The output terminal of amplifier A4 is also connected through a 100 kilo-ohm resistor R10 to the inverting input terminal of amplifier A5. The non-inverting input terminal of amplifier A5 is grounded. The output terminal of amplifier A5 is coupled back to its inverting input terminal through a 0.2 microfarad capacitor C5, and the output terminal is connected back to the inverting input terminal of amplifier A3 through a 10 milo-ohm resistor R11. The output of amplifier A5 is applied to alarm 16.

Amplifier 15 operates in known manner to amplify the output from the infrared detector 14, and the amplifier is controlled so that an output will be applied to alarm 16 only when the output from the infrared radiator 10 rises above a predetermined threshold, to indicate that the infant has stopped breathing. When that occurs, alarm 16 is activated.

Infrared radiation is produced principally by the emission of solid and liquid materials as a result of thermal excitation and by the emission of molecules of gases. Thermal emission from solids is contained in a continuous spectrum, whose wavelength distribution is described by:

$$I_\lambda d\lambda = \frac{2\pi c^2 h \epsilon \lambda}{\lambda^5} \frac{1}{e^{ch/\lambda kT} - 1} d$$

where $I_\lambda$ = spectral radiant emittance of the solid into a hemisphere in the wavelength range from $\lambda$ to $(\lambda + d\lambda)$.
c = velocity of light
h = Planck's constant — $6.62 \times 10^{-27}$ erg second
$\epsilon\lambda$ = spectral emissivity
k = Boltzmann's constant = $1.38 \times 10^{-16}$ erg/K.
T = absolute temperature of the solid emitter, K.

The spectral emissivity, $e\lambda$, is defined as the ratio of the emission at wavelength $\lambda$ of the object to that of an ideal blackbody at the same temperature and wavelength. When $\epsilon\lambda$ is unity, the foregoing equation becomes the Planck radiation equation for a black body.

Gaseous emission of infrared radiation differs in character from solid emission in that the former consists of discrete spectrum lines or bands, with significant discontinuities, while the latter shows a continuous distribution of energy throughout the spectrum.

The propagation of infrared radiation through various media is, in general, subject to absorption which varies with the wavelength of the radiation. Molecular vibration and rotation in gases, which are related to the emission of radiation, are also responsible for resonance absorption of energy. The lesser gases in the atmosphere exhibit pronounced absorption throughout the infrared spectrum. However, nitrogen and oxygen do not absorb significantly in the infrared region. Water vapor, carbon dioxide, and ozone are responsible for strong absorption in the infrared. The absorption of radiation is so prevalent that those spectral bands in which relatively little absorption occurs are identified as atmospheric windows.

Detection of the presence, distribution and/or quantity of infrared radiation requires techniques which are, in part, unique to this spectral region. The frequency of the radiation is such that essentially optical methods may be used to collect, direct, and filter the radiation. Transmitting optical elements, including lenses and windows, must be made of suitable materials, which may or may not be transparent in the visible spectrum, as shown in Table 1.

TABLE 1

| MATERIALS WHICH TRANSMIT IN THE INFRARED REGION | | |
|---|---|---|
| MATERIAL | USEFUL TRANSMISSION REGION (Micrometers) | CHARACTERISTICS |
| Optical glasses | 0.3–2.7 | Best for near-infrared |

TABLE 1-continued

MATERIALS WHICH TRANSMIT IN THE INFRARED REGION

| MATERIAL | USEFUL TRANSMISSION REGION (Micrometers) | CHARACTERISTICS |
|---|---|---|
| Fused silica | 0.2–3.5/4.5 | Some types show absorption near 2.7 micrometers |
| Arsenic trisulfide | 0.6–12.0 | A glass; subject to striations |
| Calcium aluminate | 0.3–5.5 | A glass; subject to attack by water |
| Sapphire | 0.17–6.0 | Single crystal, hard, refractory |
| Silicon | 1.1–>20 | Low density; opaque to visible |
| Germanium | 1.8–>20 | Opaque to visible |
| Sodium chloride | 0.2–15 | Water soluble |
| Potassium bromide | 0.21–27 | Water soluble |
| Lithium fluoride | 0.11–6 | Low solubility in water |
| Calcium fluoride | 0.13–9 | Insoluble |
| Thallium bromide-iodide | 0.5–40 | Moderately soft; cold flow |
| Silver chloride | 0.4–25 | Soft; cold flow |

The detector for infrared is an important component of the detection system. Photographic techniques can be used for part of the near-infrared region. Photoemissive devices, comparable to the visible- and ultraviolet-sensitive photocells, are available with sensitivity extending to about 1.3 micrometers. The intermediate-infrared region is most effectively detected by photoconductors. These elements, photosensitive semiconductors, are essentially photon detectors, which respond in proportion to the number of infrared photons in the spectral region of wavelength. This wavelength corresponds to the minimum photon energy necessary to overcome the forbidden gap of the semiconductor. All spectral regions from ultraviolet through visible, infrared, and microwaves, can be detected by an appropriately designed thermal element, which responds by being heated by the absorption of the incident radiation. In the infrared region, thermal detectors take the form of thermocouples, bolometers, and pneumatic devices. The thermal devices, in general, are not so sensitive or as rapidly responding as photoconductors. Some useful infrared detectors are listed in Table 2.

TABLE 2

REPRESENTATIVE INFRARED RADIATION DETECTORS

| DETECTOR | OPERATING TEMPERATURE (K) | USEFUL REGION (Micrometers) | TIME CONSTANT (Seconds) | FEATURES |
|---|---|---|---|---|
| Lead sulfide | 295 | Visible–2.8 | $2 \times 10^{-4}$ | Thin-film photoconductor |
| Lead selenide | 195 | Visible–5.6 | $2 \times 10^{-3}$ | Thin-film photoconductor |
| Indium/antimony | 77 | 1–5.6 | $<2 \times 10^{-7}$ | Photovoltaic crystal |
| Germanium (mercury-doped) | 25 | 1–16 | $<10^{-6}$ | Photoconductor crystal |
| Germanium (copper-doped) | 5 | 1–29 | $<10^{-6}$ | Photoconductor crystal |
| Germanium (zinc-doped) | 5 | 1–40 | $10^{-8}$ | Photoconductor crystal |
| Thermistor bolometer | 295 | All | $10^{-3} - 10^{-2}$ | Flake of mixed oxides |
| Golay cell | 255 | All | $1.5 \times 10^{-2}$ | Pneumatic |
| Thermocouple | 295 | All | $1.5 \times 10^{-2}$ | Used in spectrometers |

The infrared radiator 10 is selected of appropriate material, and is heated to a selected temperature, for example 680° K., so that the radiator will radiate infrared energy through a band shown in FIG. 4. The infrared narrow band thin film filter 12A filters out the infrared radiation shorter than 4.158 microns or longer than 4.356 microns. The thin film layer 12A, as mentioned above, is deposited on a high transmission substrate 12B which may be composed of selected quartz, sapphire, or the like which is transparent to infrared energy in the selected bandwidth.

After passing through the infrared filter 12, the infrared radiation will have a much narrower bandwidth, approximately 4.1–4.4 microns. The infrared detector 14 may be any appropriate commercially available type, such as thermopile, thermocouple, photoconductive, photovoltaic, and the like. Lead selenide or lead sulphite is appropriate for use in the infrared detector 14.

In the embodiment of FIG. 5, a hood 8A is removably mounted on a conventional crib 6A by hinged brackets 9. An alarm module 7 is mounted on top of hood 8A, the module having holes in its top and bottom, and including an appropriate circulating fan (not shown) which serves to draw the carbon dioxide emitted by the baby in the crib through the alarm module. The alarm speaker 16 is mounted on the alarm module, as well as a pair of indicator lights 17A and 17B. Indicator light 17A may be green, for example, to indicate that the system is operating, and the indicator light 17B may be red, for example, to glow when the alarm is activated. Appropriate circuitry may be incorporated into the alarm module to produce an intermittent beep of the speaker 16, and an intermittent flashing of the red indicator light 17B should the system become inoperative.

As shown in FIG. 5, the infrared radiator 10, as well as the infrared detector and amplifier 14, 15 are mounted at one end of the alarm module 7. The radiator 10 radiates infrared energy within the alarm module in all directions, and the infrared energy is incident on a spherical reflector 20 at the other end of the alarm module either directly from the radiator 10, or as a result of reflections from the sides of the alarm module.

The spherical reflector 20 reflects the infrared energy back to the detector 14, which, together with filter 12 is positioned at a distance from the spherical reflector such that all the energy reflected from the spherical reflector is incident across the surface of filter 12 and detector 14. The internal walls of the alarm unit are coated with appropriate infrared reflective material.

By use of the alarm unit 7, a "folded" optical path is used for infrared generation, absorption and detection, which greatly enhances the sensitivity of the detector 14 due to longer path geometry and internal wall reflection of the infrared rays.

In the system of FIG. 6, amplifier 15 is connected to an appropriate encoder 22 which may, for example, be a binary decimal encoder. The output signals from encoder 22 are coupled to the domestic alternating current power line through capacitors C10, C12, and through a plug 24 and socket 26.

A remote alarm 32 may then be plugged into a socket 30 at any desired location within the house. The unit 32 incorporates an appropriate decoder which responds to the coded output of encoder 22 to activate an alarm within the unit whenever the system detects that the infant has stopped breathing.

The invention provides, therefore, an apnoea monitoring system which is relatively simple and inexpensive to construct, and which is easy to operate. The system is advantageous in that it responds directly to the breathing of the infant, and does not involve any connections to the infant itself. Moreover, the system of the invention is extremely reliable in operation, and is not subject to malfunction.

While a particular embodiment of the invention has been shown and described, modifications may be made. It is intended in the claims to cover all modifications which come within the spirit and scope of the invention.

What is claimed is:

1. A monitoring system for detecting interruptions in the breathing of a monitored subject, said system including: a hood for collecting the exhaled breath of the subject; infrared radiation means for introducing infrared radiation into the exhaled breath of the subject collected in the hood so that a portion of said radiation may be absorbed by the carbon dioxide in the exhaled breath; infrared detection means for detecting the infrared radiation after it has passed through the exhaled breath of the subject; and alarm means connected to said infrared detection means to be activated upon cessation of the subject's breathing.

2. The monitoring system defined in claim 1, in which the infrared radiation means is of a selected material for infrared radiation over a predetermined wavelength range of the order of 4.250 microns–4.350 microns.

3. The monitoring system defined in claim 2, and which includes an energizing circuit for the infrared radiation means for heating the radiation means to a predetermined temperature for maximum radiation in the wavelength vicinity of 4 microns.

4. The monitoring system defined in claim 2, and which includes infrared filter means positioned in the path of the infrared radiation to said infrared detection means to limit the infrared radiation received by said infrared detection means to a bandwidth of approximately 4.1–4.4 microns.

5. The monitoring system defined in claim 1, and which includes an amplifier interposed between said infrared detection means and said alarm means to produce an activating signal for the alarm means exceeds a predetermined amplitude threshold.

6. The monitoring system defined in claim 1, and which includes an alarm module mounted on said hood, said alarm means being mounted in said alarm module, and said infrared radiation means and said infrared detection means also being mounted in said alarm module to expose the exhaled breath of the subject to the infrared radiation from the radiation means to be detected by said infrared detection means.

7. The monitoring system defined in claim 6, in which said infrared radiation means and said infrared detection means are mounted at one end of said alarm module, and which includes a spherical mirror mounted at the other end of said alarm module for reflecting infrared radiation from said infrared radiation means to direct the reflected infrared radiation to said infrared detection means.

8. The monitoring system defined in claim 1, to be used in a household, and which includes an alternating current power line, and means coupling the output of said infrared detection means to the power line, and a remote alarm unit separate from said alarm means coupled to the power line to be activated upon the cessation of the subject's breathing.

* * * * *